(12) United States Patent
Kurtz et al.

(10) Patent No.: US 6,882,739 B2
(45) Date of Patent: Apr. 19, 2005

(54) METHOD AND APPARATUS FOR RAPID GRAIN SIZE ANALYSIS OF POLYCRYSTALLINE MATERIALS

(75) Inventors: David S. Kurtz, State College, PA (US); Kryzsztof J. Kozaczek, State College, PA (US); Paul R. Moran, Port Matilda, PA (US)

(73) Assignee: HyperNex, Inc., State College, PA (US)

( * ) Notice: Subject to any disclaimer, the term of this patent is extended or adjusted under 35 U.S.C. 154(b) by 712 days.

(21) Appl. No.: 09/884,791

(22) Filed: Jun. 19, 2001

(65) Prior Publication Data

US 2003/0012334 A1 Jan. 16, 2003

(51) Int. Cl.$^7$ .................................................. G06K 9/00
(52) U.S. Cl. ........................ 382/109; 356/30; 356/335; 356/336; 378/70; 378/71; 378/73; 378/81
(58) Field of Search ............................ 382/101; 378/70, 378/71, 73, 81; 356/30, 335, 336

(56) References Cited

U.S. PATENT DOCUMENTS

| | | | |
|---|---|---|---|
| 5,724,401 A | * 3/1998 | Kurtz et al. | 378/171 |
| 5,828,724 A | 10/1998 | Kurtz | 378/70 |
| 6,005,914 A | 12/1999 | Quinn et al. | 378/81 |
| 6,038,026 A | * 3/2000 | Maris | 356/514 |
| 6,058,160 A | 5/2000 | Kurtz | 378/70 |
| 6,064,717 A | 5/2000 | Ortega et al. | 378/71 |
| 6,301,330 B1 | * 10/2001 | Kurtz et al. | 378/71 |

OTHER PUBLICATIONS

Bruker AXS Products—HI–STAR, "Hi–Star Area Detector" (http://www.esc.cam.ac.uk/new/v10/research/facilities/xray/histar.html), 1997.*

Krill et al., "Estimating grain size distributions in nanocrystalline materials from X–ray diffraction profile analysis", A Philosophical Magazine, 1998, vol. 77, No. 3, pp. 621–640.*
Abstract; Schwarzbau, H.; Equipment Measuring Surface Texture—Uses Monochromatic Radiation to Study Surface Layer of Non–Amorphous Polycrystalline Body; (1980).
Hans Joachim Bunge and Helmut Klein, Determination of Quantitative, High–resolution Pole Figures with the Area Detector, Z. Metallkd., 87 (1996) pp. 465–475.
Horst Ebel, *Crystallite Size Distributions from Intensities of Diffraction Spots*, Powder Defraction, vol. 3, No. 3, pp. 168–171 (Sep. 1998).

* cited by examiner

*Primary Examiner*—Leo Boudreau
*Assistant Examiner*—Patrick L Edwards
(74) *Attorney, Agent, or Firm*—Steven J. Hultquist; Yongzhi Yang; Marianne Fuierer

(57) ABSTRACT

An apparatus and method for performing rapid grain size analysis on a textured polycrystalline material, by generating average grain size and grain size distribution data from x-ray diffraction data of such material. Raw diffraction data is obtained by capturing a plurality of diffraction arcs within a single data capture frame. The raw diffraction data is digitally registered; (3) and the registered diffraction data is filtered to remove background noise, exclude diffraction overlaps or truncations, and compensate for biased data obtained from regions of highly preferred orientations. Average grain size and grain size distribution data are then correlated with the filtered diffraction data. The apparatus for acquiring raw diffraction data includes a collimated x-ray source having means for adjusting beam size and divergence of the x-ray generated, a 2-dimensional area detector for registering diffracted x-ray, and a sample motion assembly for moving the sample in the sample plane. The resulting system is fast, accurate, amenable to automation, and does not require highly skilled personnel to operate.

44 Claims, 7 Drawing Sheets

METHOD AND APPARATUS FOR RAPID GRAIN SIZE ANALYSIS OF POLYCRYSTALLINE MATERIALS

FIELD OF THE INVENTION

The present invention generally relates to the field of crystallographic structure analysis, and more specifically relates to crystallite grain size analyzing method and apparatus for determining average grain size and grain size distribution of polycrystalline materials.

BACKGROUND OF THE INVENTION

Optimization of average grain size and grain size distribution is important for many commercial products utilizing advanced materials. Advanced materials can be found in semiconductor and electronic devices, high power components, structural alloys and ceramics, and high performance coatings. Grain size and grain size distribution is particularly critical for improving performances of semiconductor materials.

Conventional grain size analysis utilizes techniques such as micrograph image analysis, which is often referred to as metallography. The micrograph image analysis is generally performed upon micrographs of carefully polished and preferentially etched polycrystalline samples. However, the polishing and etching processes are very destructive to protective layers over-coating the samples. Moreover, the micrographs so taken reflect merely 2-dimensional cross-sectional views of the 3-dimensional crystal grains, rendering determination of grain size based thereupon inaccurate. Finally, the resolution limits of the equipments currently available render the micrograph image analysis suitable only for materials with relatively large grains, usually above 5 microns.

More recently developed grain size analysis techniques employ electron backscatter diffraction (EBSD) and focused ion beam (FIB) systems to measure grain sizes as small as about 0.25 microns. Although these new techniques are more accurate than the conventional micrograph image analysis, they are slow and tedious to carry out, because they can measure only one grain at a time. In order to obtain statistically accurate analysis results, a reasonably large number of grains have to be analyzed one by one, and conducting a complete analysis is therefore too slow for practical on-line quality control applications. Moreover, the EBSD and FIB techniques both require destructive polishing and cleaning, and they also measure only cross-sectional areas of the grain, not its full volume.

Ultrasonic and optical reflection techniques have also been used to estimate average crystallite size by using a calibrated sample. However, measurements obtained by such techniques are easily distorted by variation in numerous non-relevant material properties of the polycrystalline samples, such as phase composition crystallographic texture, residual stress, porosity, etc. Therefore, the ultrasonic and optical reflection techniques cannot accurately measure average grain size unless all other material properties are always constant, which rarely happens. These techniques are not capable of measuring grain size distribution.

X-ray diffraction (XRD) techniques have also been used to determine the relative crystallite size and size distribution of a polycrystalline material. A beam of monochromatic x-rays, when directed to a polycrystalline material surface, scatters in all directions. The scattered x-rays in certain directions interfere and reinforce each other, resulting in diffraction peaks (i.e. intensity maxima) in such directions. Each particular set of crystalline planes (hkl) of a grain has an associated diffraction peak that occurs at a particular angle. Therefore, the diffraction image provides direct information about the total number and spacing of individual crystal grains that comprise the polycrystalline material. Based on such information, average grain size and grain size distribution can be determined.

Peak broadening analysis, which is also referred to as line profile analysis or line broadening analysis, is a commonly used x-ray diffraction method for determining relative crystallite size. This method observes the change in peak width of an x-ray diffraction peak for a particular (hkl) crystallographic plane. A diffraction peak typically results from a large number of grains of different sizes within the irradiated area on the sample satisfying the Bragg diffraction condition. As the average grain size decreases, the x-ray diffraction peak width (i.e. the distance between two adjacent diffraction peaks) increases, and thus peak width can be used to measure the relative change in average grain size.

However, the peak broadening analysis is suitable only for analyzing polycrystalline materials with grain sizes generally below 0.1 micron. It is inadequate when the polycrystalline materials to be measured have grains of larger sizes. Moreover, the diffraction peak width can be significantly affected by variation in irrelevant factors such as instrument broadening effects (i.e. focusing precision of the x-ray optics), crystallographic texture, and presence of faults in crystallographic structure including dislocations. The peak broadening analysis is effective only under tightly controlled comparative analysis conditions, which require very similar sample compositions and cold work levels with measurements conducted on the same instrument. Therefore, the peak broadening analysis is of very limited use for most advanced thin film materials that have widely varying compositions and grain sizes (commonly >0.1 micron), substantial degree of texture, and residual micro and macro-strains.

Another less common x-ray diffraction method for grain size analysis involves the analysis of "spot" reflections from individual grains, which are bright spots formed on x-ray film or a two-dimensional detector by diffracted x-rays with high intensity. This x-ray diffraction method has been referred to as spot count analysis. Generally, a correlation exists between the total number of such bright spots counted with a known total irradiated volume and the average grain size of the sample material, assuming that each spot is formed by x-ray diffracted by an individual grain. It is also well established that the spot intensity is proportional to the size of the grain from which the x-ray is diffracted. Thus, the distribution of spot intensities can be correlated to the distribution of grain sizes.

The spot count analysis is limited in practice to a certain grain size range due to resolution and sensitivity limits of equipment used, and is usually only suitable for analyzing materials with grain sizes above 1 micron. Although a paper by Horst Ebel entitled "Crystallite Size Distributions from Intensities of Diffraction Spots", POWDER DIFFRACTION, Vol. 3, No. 3, September 1988, pp. 168–71, states that the spot count analysis theoretically can analyze non-textured polycrystalline material with crystallite size as small as 0.1 micron, actual data presented by this paper are only for aluminum powders with sizes ranging from 9.5 to 11 microns. Moreover, accuracy of the spot count analysis is also adversely affected by the presence of any crystallographic texture. As the texture increases, more crystal grains tend to orient themselves in just a few highly preferred orientations, which results in overlapping of spot reflections on several predominant regions on the x-ray film, making it more difficult to resolve spots in these regions. Furthermore, the correlation between the number of spots counted within the known irradiated volume and the average grain size can be complicated by the presence of crystallographic texture. The spot analysis technique therefore can only be used to analyze completely non-textured fine spherical powders, with completely random crystal orientations. There are no known practical solutions as to how the spot analysis technique can be used for analyzing continuous polycrystalline materials with any degree of texture and/or residual stress present, nor as to how such technique can be used to provide grain size distribution information.

It therefore is one object of the present invention to provide a method and apparatus for rapid determination of average grain size and grain size distribution in polycrystalline materials with widely varying grain sizes (from about 0.1 micron to about 100 microns) and varying amounts of crystallographic texture and residual stress.

It is another object of the invention to provide a system enabling sufficiently rapid grain size measurement to allow automated grain size analysis production quality control in commercial processing operations.

A further object of the present invention is to provide a grain size analysis system that can be operated in a production environment, and by persons without specialized skill or training.

Other objects and advantages will be more fully apparent from the ensuing disclosure and appended claims.

SUMMARY OF THE INVENTION

The present invention achieves effective grain size analysis for textured polycrystalline materials through the use of a unique and innovative integral grain size analysis protocol, comprising the steps of:

(a) digitally registering raw diffraction data obtained by detecting radiation energy diffracted from a sample to capture a plurality of diffraction arcs within a single data capture frame;

(b) filtering the registered diffraction raw data to remove background noise, exclude diffraction overlaps or truncations, and compensate for biased data obtained from regions with highly preferred orientations;

(c) correlating average grain size and grain size distribution data with the filtered diffraction data.

This grain size analysis protocol enables quantitative grain size analysis on materials exhibiting variation in material properties such as texture and residual stress, by both filtering out data highly affected by such variation, and mathematically factoring in the presence of such variation while correlating average grain size and grain size distribution with diffraction data. The new analysis protocol itself can be extended to any polycrystalline material in many different product forms. Although semiconductor wafer analysis is one preferred application of the present invention, it is not thus limited and can be used in many other applications, such as grain size analysis in reel-to-reel fabrication processes, and heat treatment steps of polycrystalline materials.

The present invention also significantly reduces the data acquisition time required, by employing a collimated source of monochromatic radiation energy, for directing radiation energy to a measurement point on a sample, and a 2-dimensional area detector for registering radiation energy diffracted from the measurement point, with the collimated source of radiation energy and the 2-dimensional area detector being in a fixed spatial relationship to each other and sufficiently proximate to the sample measuring point to capture a plurality of diffraction arcs within a single data capture frame of the detector.

The use of an area x-ray detector, as opposed to the point source detectors traditionally used for texture mapping, greatly reduces data acquisition time by capturing a relatively large range reciprocal space, and storing it as a digitized electronic file. Multiple diffraction arcs can thus be captured in a single detector frame, both reducing data acquisition time and increasing accuracy.

Another feature of the present invention is that the x-ray beam source and area x-ray detector are arranged in carefully chosen fixed spatial locations, which determine correspondingly fixed ranges of sample coverage in $2\theta$ and $\chi$ directions (see FIG. 10). Conventional x-ray diffraction systems require movement of the detector in the $2\theta$ direction and movement of the sample in the $\chi$ direction in order to obtain a sufficiently large number of diffraction spots for purpose of analyzing grain size. In contrast, the present invention, by fixing the spatial relationship between the x-ray beam source and area x-ray detector, fixes the sample coverage in $2\theta$ and $\chi$ directions and thus eliminates motion of the detector and sample in these two directions.

Moreover, such fixed spatial locations between the x-ray beam source and area x-ray detector are optimally integrated with a particular set of sample motions (usually planar motion within the sample plane defined by the sample holding device in order to obtain suitable texture information required for the grain size analysis), and optimally integrated with a primary set of materials that the inventive system is used to analyze. This enables the elimination of the conventional Eulerian cradle used to rotate the sample in the $\chi$ direction, the $\theta$ rotating stage used to rotate the sample, and the $2\theta$ rotating stage used to rotate the detector, as required in the prior art systems to obtain a statistically sufficient number of grain counts. Elimination of these motion stages greatly simplifies the system and significantly reduces its cost.

A specific aspect of the present invention relates to a method of determining average grain size and grain size distribution of a polycrystalline material, comprising:

providing a sample comprising the polycrystalline material;

irradiating a measurement point on the sample with radiation energy generated from a monochromatic radiation source, wherein the beam size and divergence of the radiation energy is adjusted so that an adequate number of crystal grains of the sample is irradiated by the radiation energy;

detecting radiation energy diffracted from the sample to capture a plurality of diffraction arcs within a single data capture frame; and generating average grain size and grain size distribution data from the diffraction data of the detected diffracted radiation energy, according to an integral grain size analysis protocol comprising the steps of:

(a) digitally registering raw diffraction data from the plurality of diffraction arcs captured;

(b) filtering the registered diffraction data to remove background noise, exclude diffraction overlaps or truncations, and compensate for biased data obtained from regions with highly preferred orientations; and (c) correlating average grain size and grain size distribution data with the filtered diffraction data.

In the present application, the phrase "an adequate number of crystal grains" refers to an approximate range of about 50 to about 5000 grains lying within the irradiated area.

Another aspect of the present invention relates to a system for determination of average grain size and size distribution of a polycrystalline material. The system comprises:

a sample comprising the polycrystalline material and defining an associated sample plane;

a collimated source of monochromatic radiation energy directing radiation energy to a measurement point on the sample, wherein the collimated source comprises means for adjusting beam size and divergence of the radiation energy;

a 2-dimensional area detector that registers radiation energy diffracted from the sample at the measurement point, with the collimated source of radiation energy and said 2-dimensional area detector being in a fixed spatial relationship to one another and sufficiently proximate to the sample measuring point to capture a plurality of diffraction arcs within a single data capture frame of the detector;

a sample motion assembly translating the sample in the sample plane; and an integral grain size analysis processor constructed and arranged to generate average grain size and grain size distribution data from the detected diffraction data of the diffracted energy.

Preferably, the integral grain size analysis processor comprises computational means for:

(a) digitally registering raw diffraction data from the plurality of diffraction arcs captured;

(b) filtering the registered diffraction data to remove background noise, exclude diffraction overlaps or truncations, and compensate for biased data obtained from regions of highly preferred orientations;

(c) correlating average grain size and grain size distribution data with the filtered diffraction data.

The invention enables fast, efficient, and accurate analysis of average grain size and grain size distribution for continuous polycrystalline materials in bulk, thin film, film stack, particulate or other forms, with widely varying grain size, crystallographic texture, and residual stress.

DETAILED DESCRIPTION OF THE INVENTION AND PREFERRED EMBODIMENTS THEREOF

The present invention relates to an apparatus and method of measurement enabling rapid and accurate determination of average grain size and grain size distribution for polycrystalline materials with widely varying grain size, crystallographic texture, and residual stress.

Figure 9:
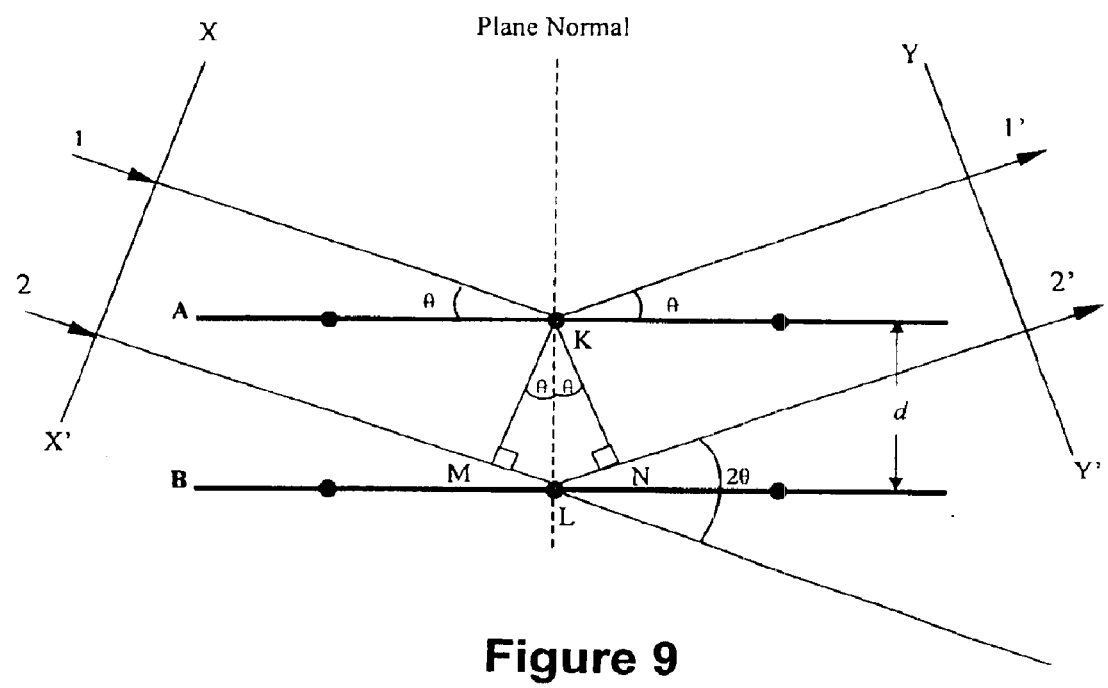
FIG. 9 is a schematic representation of the x-ray diffraction condition under Braggs Law.
Figure 10:
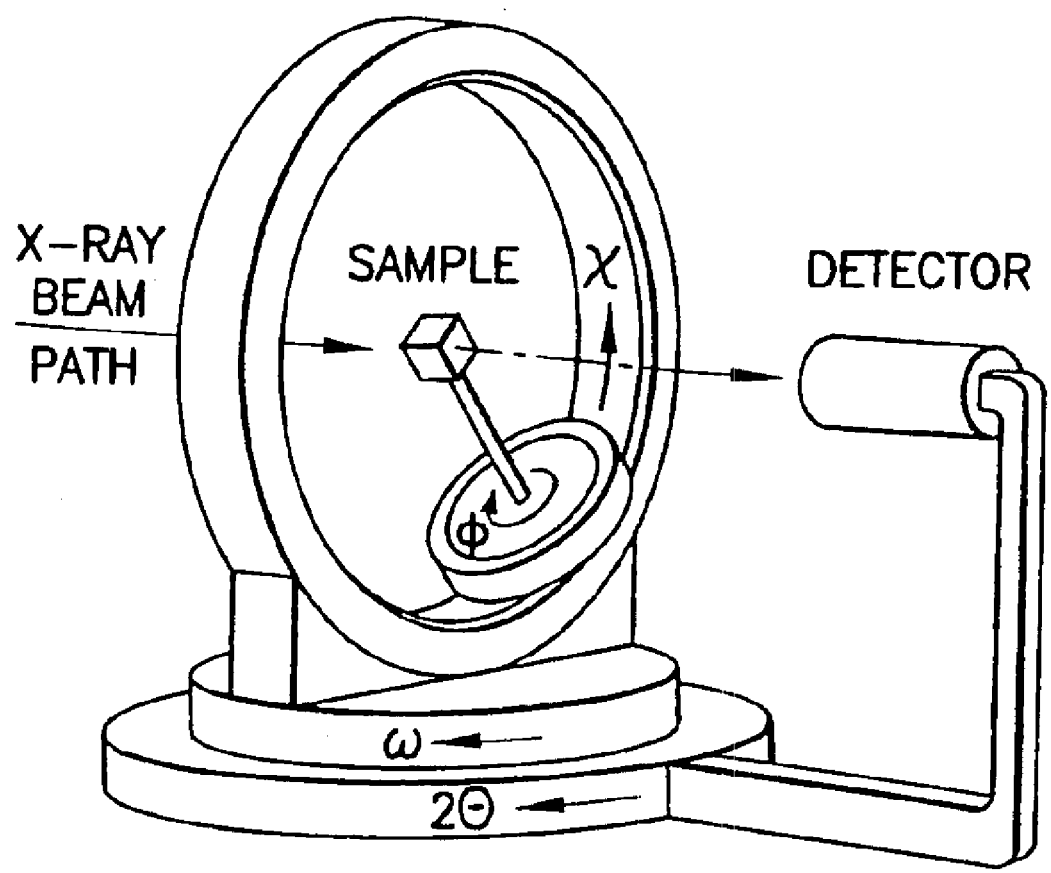
FIG. 10 is a perspective depiction of various rotation directions around a crystalline sample to be measured.

Generally, when a monochromatic, nearly parallel x-ray beam interacts with a single crystal, x-rays will scatter in all directions. The scattered x-ray intensity in certain vector directions will be much higher due to constructive interference between the incident x-ray beam and specific crystallographic planes within the crystal. FIG. 9 shows a schematic representation of a section of a crystal, having its atoms arranged on a set of parallel planes A and B that are normal to the plane of the drawing and spaced a distance d apart. Assume that a beam of perfectly parallel, perfectly monochromatic x-rays (shown as rays 1 and 2) of wavelength $\lambda$ is incident on this crystal at an angle $\theta$, which is commonly referred to as Bragg angle, wherein $\theta$ is measured between the incident beam and the particulate crystal planes (hkl) under consideration. Rays 1 and 2 strike atoms K and L on crystal planes A and B, respectively, and are scattered by such atoms (represented by scattered rays 1' and 2'). The path difference for rays 1-1' and 2-2' is ML+LN, assuming XX' and YY' are the wave fronts of these rays. Knowing that KL=d, and the angles between KL-KM and KL-KN equal $\theta$, it is evident that $$ML + LN = d \sin \theta + d \sin \theta = 2d \sin \theta$$

Scattered rays 1' and 2' will be completely in phase and therefore reinforce each other to generate a high intensity x-ray signal, only if the path difference between them is equal to a whole number n of wavelengths of such rays, which is referred to as Bragg condition, as follows:

$$n\lambda = 2d \sin \theta$$

In a polycrystalline material, a monochromatic, generally parallel x-ray beam will strike many thousands of grains at a time. Each grain will contain the same group of (hkl) planes, but the orientation of those planes with respect to some reference vector (typically the vector normal to the sample surface) can be different for each grain. In other words, each grain can have a different orientation. Hence, a large percentage of those grains will not meet the Bragg condition for particular (hkl) planes and therefore do not contribute to diffraction signal. Only those grains that meet the Bragg condition will scatter the incident x-ray beam in a manner that the scattered x-ray beams from different crystal planes reinforce each other to cause a diffraction pattern with discontinuous, high intensity x-ray spots.

The diffracted x-rays from a particular set of (hkl) planes, originating from many different grains, are oriented in a series of directions that form a cone emanating from the irradiated spot. All points on this cone correspond to a single (hkl) crystallographic plane, but can come from grains with different orientations. This is schematically shown in FIG. 1.

Figure 1A:
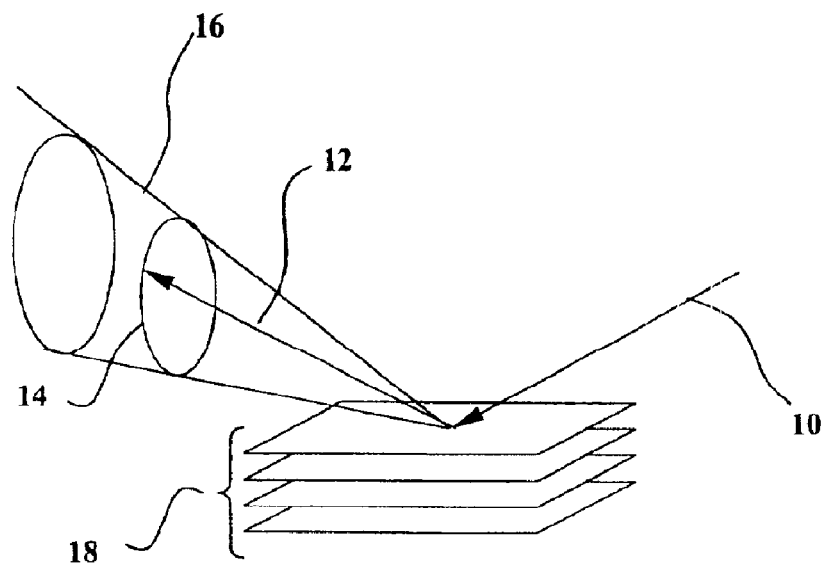
FIGS. 1A and 1B are schematic representations of two sets of crystalline planes that diffract a beam of incident monochromatic x-rays in different directions, forming a diffraction cone.
Figure 1B:
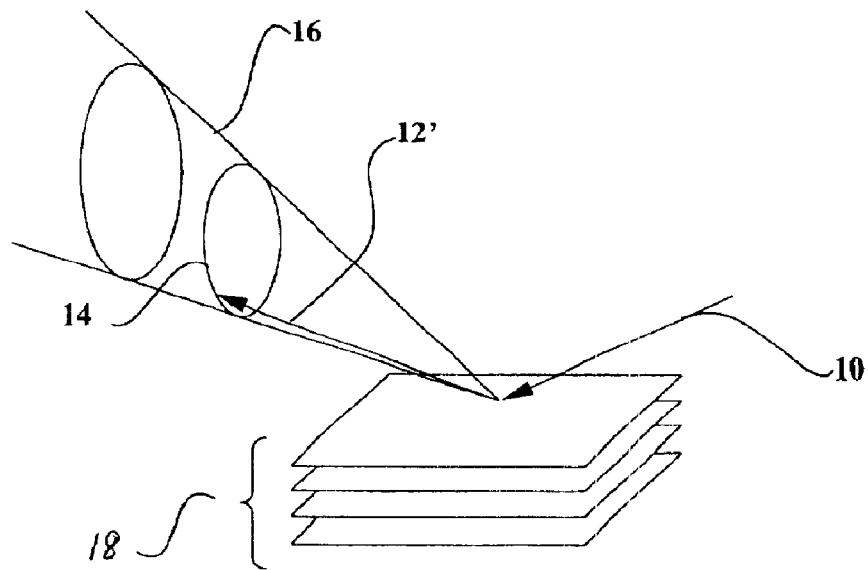

In FIG. 1A, a particular set of crystal planes 18 within a given grain, when irradiated by an incident x-ray beam 10, gives rise to a diffracted beam vector 12, forming a single spot of high intensity, assuming that planes 18 meet the Braggs condition. FIG. 1B shows another crystal grain with the same set of crystal planes 18 in a different orientation, which still meet the Bragg condition. The crystal planes 18 in FIG. 2, when irradiated by the same incident x-ray beam 10, gives rise to a diffracted beam vector 12' at a different direction. The collection of many diffracted beam vectors similar to 12 and 12' creates a diffraction cone 16 emanating from the irradiated spot.

Figure 5:
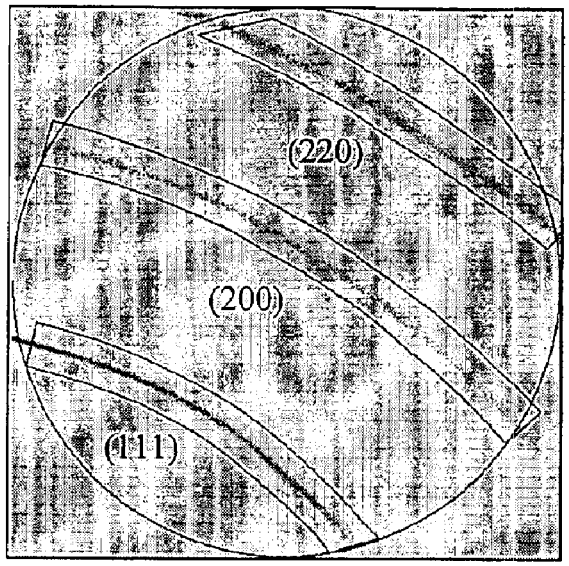
FIG. 5 is a segmental x-ray diffraction pattern of a thin copper film having relatively small grain size.
Figure 6:
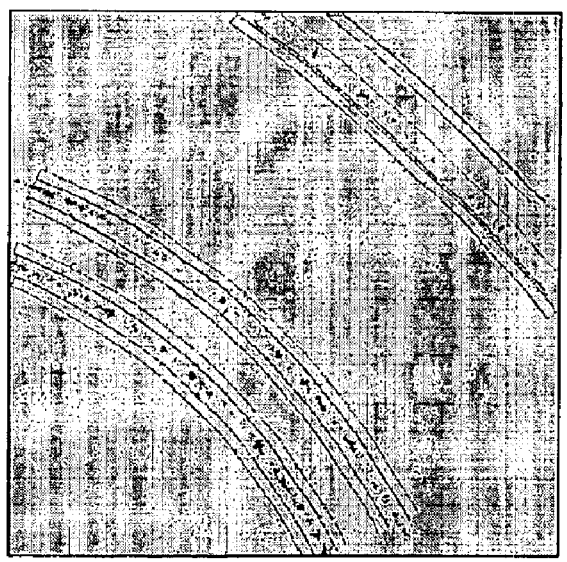
FIG. 6 is a segmental x-ray diffraction pattern of another thin copper film having relatively large grain size.
Figure 7:
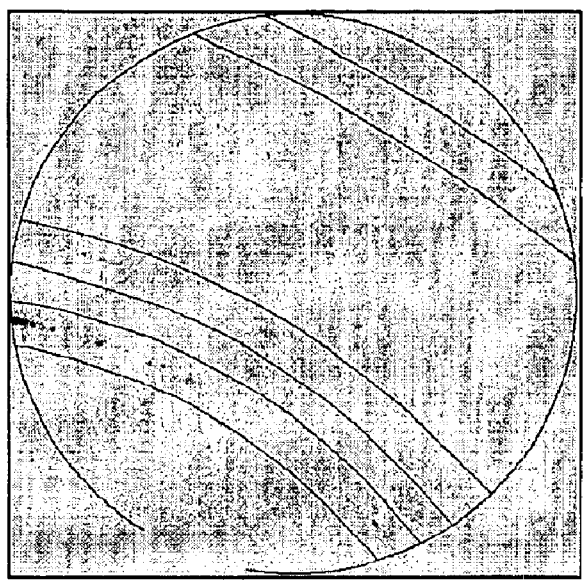
FIG. 7 is a segmental x-ray diffraction pattern of another thin copper film with significant <111> texture.

Each diffraction cone 16 results from one particular set of crystallographic planes (hkl) 18 which meets the Bragg condition, while each cone 16 contains a large number of spots on different locations of the cone. Such spots are formed by diffracted beam vectors 12 and 12' generated by many randomly oriented grains within the irradiated volume. Using a two-dimensional x-ray imaging device, a diffraction image can be obtained with multiple Debye rings 14, which represent planar slices through multiple diffraction cones. FIGS. 5–7 are all diffraction images taken for thin copper films, showing fractions of Debye rings formed by crystallographic planes (111), (200), and (220).

If the incident beam size is too large relative to the grain size of the polycrystalline material being analyzed, a large number of individual diffraction spots generated by individual grains within the irradiated area essentially blend together, forming a continuous Debye ring, as shown by FIG. 5. It is simply impossible to count individual spots in such a continuous ring.

As the size of the incident beam decreases, the number of grains within the irradiation area decreases as well, and the Debye ring transitions from a continuous ring with overlapping spots into a discontinuous ring of discrete spots, as shown in FIG. 6. The number of grains within the irradiated area now is small enough to result in observation of individual diffraction spots from individual grains. Thus, it is necessary to reduce the incident beam size until spots are clearly resolved.

By using a collimator to adjust the incident beam size, one can optimize diffraction images for many different materials of various grain sizes to obtain desired discontinuous Debye rings. Ideally, the collimator employed is small enough to resolve spots of most of the polycrystalline materials analyzed, but not too small as to limit the number of spots observed at the irradiated sample location, because accuracy of the grain size analysis depends on obtaining a statistically sufficient number of grains within the irradiated area. Moreover, as the collimator size is reduced to resolve smaller and smaller grains, the intensity of the diffraction spots generated by the small grains eventually drops down to the same level as the background x-ray noise, and such spots are no longer resolvable.

When texture is present in the polycrystalline sample material, a large percentage of the grains are oriented in several preferred orientations, and the Debye rings will correspondingly exhibit much higher intensity in one region than another, and the spots observed for individual grains will meld into a single high intensity zone in the region of preferred orientations, as shown by FIG. 7 (highly preferred orientation region is circled in white). Grains that are not oriented in this preferred direction will appear as individual spots outside of the highly preferred orientation region. Such individual spots are still suitable for grain size analysis, if regions of highly preferred orientation are excluded from the spot analysis. Moreover, the quantitative analysis of texture in the sample can be provided in order to correlate the grains counted within a limited section of the Debye ring with the average grain size, if such section has sufficiently random orientations.

Figure 3:
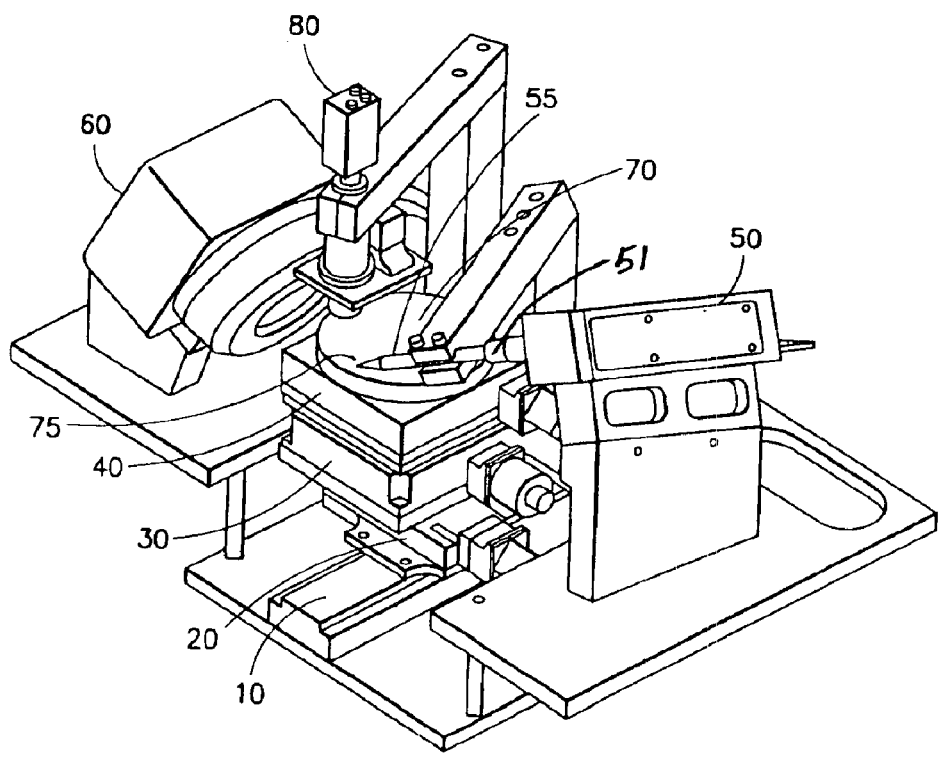
FIG. 3 is a perspective depiction of the essential components of the apparatus of the present invention applied to the analysis of semiconductor wafers, and of their spatial arrangement.

An example of the present invention applied to grain analysis for semiconductor manufacturing is shown in FIG. 3. The apparatus of the present invention utilizes an x-ray source with collimation device and an area x-ray detector with its positioning optimized for a particular range of coverage within reciprocal space.

The apparatus preferably comprises three interacting components: the collimated x-ray source components, the sample handling apparatus, and the area detector. The x-ray area detector 60 is mounted to a rigid base. Also mounted to the rigid base are the sealed x-ray beam source 50, monochromator 51, and x-ray collimator 55. In this particular example useful for semiconductor manufacturing, the sample handling apparatus consists of a wafer motion apparatus, having a y-stage 10, an x-stage 20, a z-stage 30, and a φ-stage 40. Also shown is an optional video microscope 80. The example application of the invention is primarily designed to handle semiconductor wafers 70 up to 300 millimeters in diameter, but the apparatus can be readily modified to handle larger or smaller wafers.

A preferred aspect of the invention is that it fixes the x-ray source and detector in specific spatial locations. The sample handling apparatus is mounted in such a way to not spatially interfere with the x-ray source, collimator or detector, but allow sample motion sufficient to cover all locations of the sample surface, and to also allow in-plane rotation at all of these locations. In the example configuration for semiconductor wafer processing, the wafer motion stages are arranged in the following order from top to bottom: φ rotation, z (vertical) motion, x linear motion, and y linear motion. These wafer motions are configured in such a way as to allow full wafer motion, as well as close proximity of the area detector to the wafer measure point 75.

Although described hereinafter with reference to a preferred application of the invention for semiconductor wafer analysis, in which a sample motion assembly comprising three mutually orthogonal rectilinear translational motion stages is operatively coupled to a rotational motion stage, it will be appreciated that the invention may be alternatively advantageously practiced with other sample motion-effecting means, such as sample translation robots, reel-to-reel winding systems, dynamic motion support structures, etc., which provide appropriate nature and extent of movement of the sample for analysis.

Figure 4:
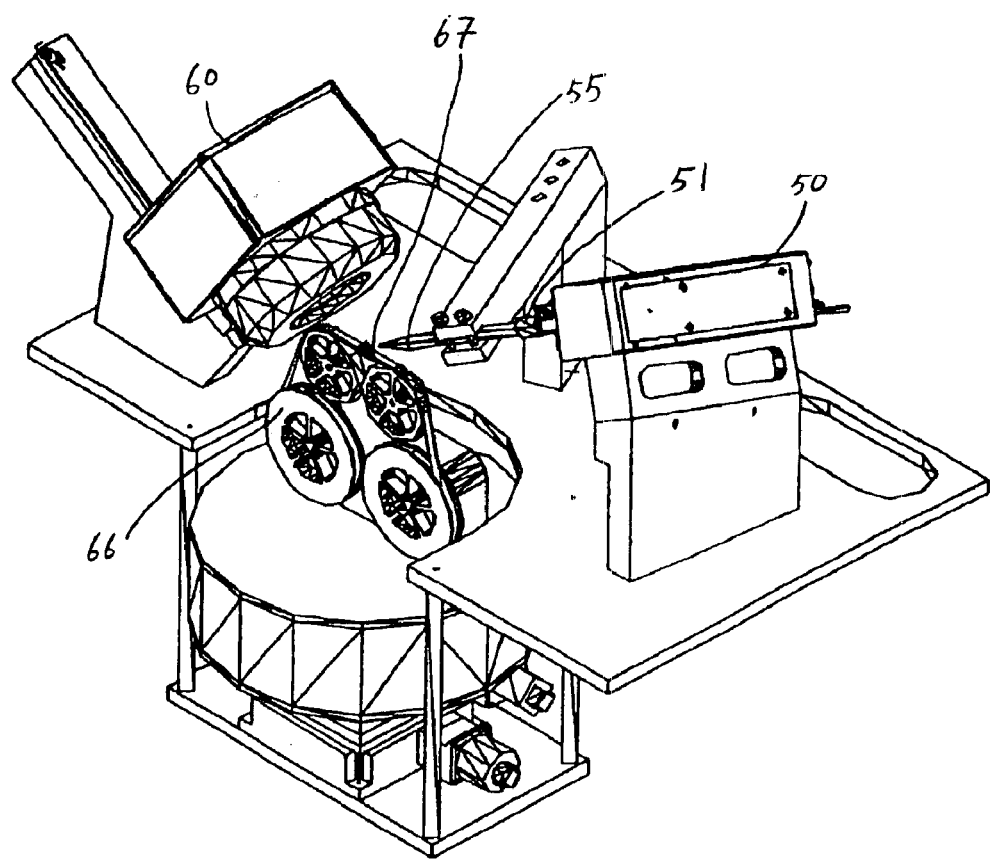
FIG. 4 is a perspective depiction of the apparatus in FIG. 3 applied to the analysis of superconducting tape fed through a reel-to-reel system, and of their spatial arrangement.

For instance, the apparatus of FIG. 3 can be used in analyzing a superconducting tape 67 fed through a reel-to-reel winding system 66, as shown in FIG. 4.

In one example, the sample motion-effecting means effectuates planar motions-movements in the plane of the sample. The sample can be in the form of a thin wafer or other planar structure, defining a corresponding sample plane. The movements of the sample for the analysis are in this sample plane, and the sample is not rotated out of the sample plane for texture analysis; rather, all sample movements are "in-plane" movements, as effected by the sample motion assembly.

In a more complex example, the sample is not planar, and the sample motion-effecting means effectuates non-planar motions in order to keep the measuring point 75 (see FIG. 2) in a constant plane.

The apparatus of the present invention as applied to semiconductor wafer analysis dispenses with the Eulerian cradle that provides sample rotation in $\chi$ direction, and the θ–2θ goniometer, of prior art analysis systems used for measuring crystallographic texture, which is used in this invention as part of the protocol for determination of average grain size and grain size distribution. These prior art motion stages force the area detector to be placed at a larger distance from the measurement spot, in order to enable full motion of the wafer. The increased distance between the area detector and the measurement spot results in a smaller angular image range covered by the area detector, hence leads to slower analysis of crystallographic texture, with more sequential rotations, and much less angular range of $\chi$ and 2θ at each detector position. The added stages also considerably increase the cost and complexity of wafer motion.

In the present invention as applied to semiconductor wafer analysis, the fixed ranges of 2θ and $\chi$ are optimized for a group of specific material systems, by placing the detector 60 and x-ray source 50 at very specific permanent locations. By capturing a desired set of crystallographic reflections over a preferred range of $\chi$ for each reflection, the maximum amount of texture information can be extracted from the measurement process through a new and more efficient analysis.

Figure 2:
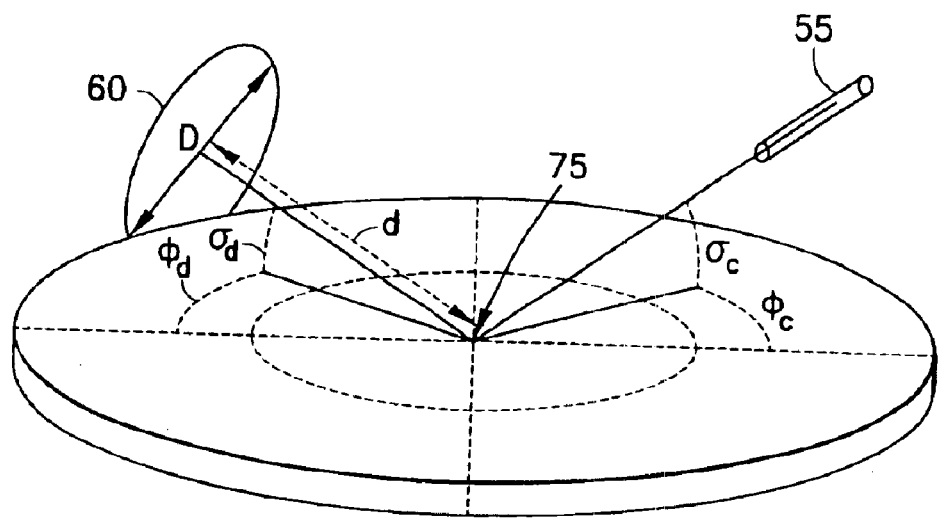
FIG. 2 is a schematic representation of the geometry between the x-ray source, the sample under measurement, and the area x-ray detector.

The geometry between the x-ray source, the area detector, and the sample is herein illustrated in FIG. 2. The polar angle, $\sigma_c$, and the azimuthal angle, $\phi_c$, determine the position of the x-ray source, the angles $\sigma_d$ and $\phi_d$ determine the position of the detector, d is the detector to sample distance, and D is the detector diameter.

In the case where the detector normal and x-ray beam coincide on the wafer plane, the geometry is described by 6 parameters: 2 angles for the x-ray source, 2 angles for the detector, detector radius, and distance to sample. Those 6 parameters are optimized in such a way that the regions covered provide the necessary and sufficient data for grain size and size distribution analysis.

A Hi-Star® multiwire gas proportional counter, produced by Bruker AXS, Madison, Wis., is currently a preferred area x-ray detector suitable for grain size analysis in polycrystalline materials. It offers high sensitivity combined with a large total circular detection area that is 11.5 centimeters in diameter. Any other suitable two-dimensional type area detector with sufficient angular range and spatial resolution can be employed, including, but not limited to, x-ray image charge-coupled device (CCD) cameras, x-ray image plates, and other 2-D x-ray detectors. Preferably, such area detector has large area, high sensitivity, and a mechanism for rapid transfer of data to electronic digital format.

Total reflection tapered capillary collimators are preferably employed for adjusting beam size and divergence of the x-ray generated by the x-ray source, to provide a higher x-ray flux than traditional pinhole collimators. Other collimation devices can also be used for purpose of practicing the present invention, including polycapillary optics, multireflection mirrors, pinholes, cross-oriented slits, etc.

The x-ray source can be a standard monochromatic sealed beam tube, a rotating anode, or any other suitable source for generating monochromatic x-rays. A high intensity x-ray source would be preferred for analysis processes conducted on polycrystalline materials with very small grain size and/or weakly diffracting materials.

Additional information concerning the apparatus arrangement, is contained in co-pending (now allowed) U.S. application Ser. No. 09/365,063 for "Apparatus and Method for Texture Analysis on Semiconductor Wafers" filed Jul. 30, 1999 and issued as U.S. Pat. No. 6,301,330 on Oct. 9, 2001, the contents of which are herein incorporated by reference in their entireties for all purposes. The apparatus disclosed in such co-pending application allows in-plane rotation of the sample about a single measurement spot. Therefore, diffraction data can be collected at sequential rotations in order to obtain a large number of different grains, or spots for grain size analysis while simultaneously collecting the required data for texture analysis.

The rotation capability also provides another advantage for improved grain size analysis. By rocking the sample in the in-plane direction by any amount less than or equal to the divergence of the x-ray beam, the imperfection of the crystal grains is better matched to the divergence of the beam, resulting in a more intense spot with an improved Gaussian shape. In one preferred embodiment, a 100 micron collimator is used to form a beam with a divergence in the vicinity of about 0.3° with an in-situ rocking of the sample within ±0.1°.

The present invention achieves rapid and accurate grain size analysis, by performing an integral grain size analysis protocol using diffraction data obtained from the apparatus of the invention. Such grain size analysis protocol specifically comprises the steps of: (a) digitally registering raw diffraction data from the plurality of diffraction arcs captured; (b) filtering the registered diffraction data to remove background noise, exclude diffraction overlaps or truncations, and compensate for biased data obtained from regions with highly preferred orientations; and (c) correlating average grain size and grain size distribution data with the filtered diffraction data.

First, raw diffraction data comprising Debye ring segments obtained from the area detector are acquired and stored. Any of the multiple (hkl) reflections present within the detector image can be analyzed. In order to register a sufficient number of spots at any sample location, the sample can be rotated in the sample plane with the center of rotation coinciding with the irradiated measurement spot. During data acquisition, quantitative texture analysis can also be performed in the same measurement sequence, according to the procedure disclosed in U.S. application Ser. No. 09/365, 063, which has been issued as U.S. Pat. No. 6,301,330. The quantitative texture information can be later factored in, to achieve accurate grain size analysis for polycrystalline materials with a significant degree of texture.

Figure 8:
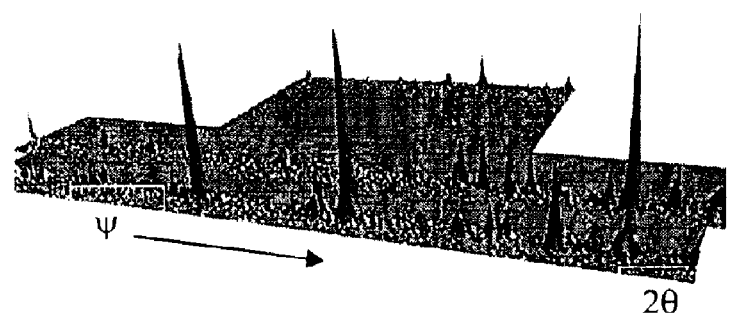
FIG. 8 is a three-dimensional surface plot of x-ray diffraction data for three Debye rings from which the curvature has been mathematically removed, with diffraction intensity for each ring represented by a series of spots, each spot represented by height of a spike at such spot.

In order to facilitate the subsequent filtering and correlating steps, the raw diffraction data, usually in form of spot intensity distribution image, are digitally registered and then converted from $\chi$ and 2θ coordinates to x and y coordinates with an intensity registered at each x and y location. The converted spot intensity distribution image can then be outputted in a three-dimensional surface plot form, of the type shown in FIG. 8. Each spot appears as a spike positioned along each Debye ring, with the diffraction intensity of each spot registered as the height of the corresponding spike. Alternatively, each spike is fitted with a standard distribution function, and the diffraction intensity is set to be equal to the volume of such function.

The digitally registered diffraction intensity distribution image then is filtered through a specific set of criteria to generate a set of grain size distributions and grain count. The filtering process is critical in the practice of the present invention, especially at the lower grain size ranges, when background x-ray noise and overlapped or truncated diffraction spots would otherwise substantially adversely impact accuracy of the data.

In a preferred embodiment of the present invention, a three-dimensional peak-searching algorithm is employed to search for local intensity maxima that meet a threshold intensity criterion. Such algorithm counts only those spots with intensity above the threshold intensity, and thus eliminates those spots that are considered as background x-ray noise. This maxima count can be specified for a certain $\Delta\theta$ range across the Debye ring, and used as the total grain count of the region of the Debye ring that is being analyzed.

Additionally, the filtering process can employ an algorithm for fitting a two-dimensional Gaussian curve, or any other suitable standard distribution function, to the maxima count obtained in the previous step. Criteria of fitting a Gaussian curve or other standard distribution functions effectively excludes adjacent spots with excessive intensity overlaps (which are generated by crystal grains with nearly identical orientations) or spots that are significantly truncated (which are generated by crystal grains that are only partially within the $\Delta\theta$ range or the irradiated volume). This step is important for achieving high accuracy in the grain size distribution determination, where an accurate measure of the integrated diffraction intensity from each crystal grain is directly related to the size of such grain.

Moreover, the filtering process can comprise a step for excluding biased data obtained from regions with highly preferred orientations. Such data are generally irresolvable, due to the fact that diffraction peaks of many crystal grains with the very similar orientations are excessively overlapped and can be mistaken as one large grain, reducing the accuracy of the analysis results.

The filtered spot intensity distribution data then can be correlated to average grain size and grain size distributions, using one of the following two approaches.

The first approach is a simple calibration process, which provides a set of standard polycrystalline samples with known average grain size and grain size distribution (measured by EBSD or FIB techniques). The filtered diffraction intensity distribution of the sample being characterized is then compared/calibrated against the diffraction intensity distribution of the standard calibration samples, to generate corresponding average grain size and grain size distribution for the sample being characterized. Such calibration method provides a quick determination of average grain size and grain size distribution.

A second alternative approach analytically correlates average grain size and grain size distributions with diffraction data, without requiring standard calibration samples; rather, it relies on the following correlation steps:

(a) estimating total number of grains within an irradiated volume of the sample;

(b) calculating average grain size from the total number of grains within the irradiated volume; and (c) converting the intensity distribution into grain size distribution, based on the average grain size calculated.

Specifically, the number of grains ($\Delta N$) within a $\Delta\theta$ section of a Debye ring, in comparison to the total number of grains (N) within the complete diffraction sphere, is given by:

$$\Delta N/N = \cos\theta \times \Delta\theta \times p/2 \quad \text{(Equation 1)}$$

$$\rightarrow N = 2\Delta N/(\cos\theta \times \Delta\theta \times p) \quad \text{(Equation 2)},$$

in which p is the multiplicity factor of the crystalline planes used for analysis. With $\Delta N$, $\theta$, $\Delta\theta$, and p already known from the filtered diffraction data, N can be determined. Since the total number of grains within the complete diffraction sphere equals the total number of grains within the irradiation volume, the value of N is actually the total number of grains within the irradiation volume.

However, equations 1 and 2 only apply if the sample in question is randomly oriented, while the vast majority of continuous polycrystalline materials have same degree of texture and thus are not randomly oriented. Therefore, it is necessary to modify such equations to factor in the presence of texture.

The following modified equation more accurately reflects the total number of grains within the irradiated volume of a textured polycrystalline sample:

$$N = 2\Delta N \times \alpha \times f/(\cos\theta \times \Delta\theta \times p) \quad \text{(Equation 3)},$$

In which f is the probability of grains being in the a fraction of the Debye ring, determined by the following equation:

$$f = (\int_\alpha PF\, d\alpha) \quad \text{(Equation 4)},$$

wherein PF is the pole density that occurs within the $\alpha$ fraction of the Debye ring.

With both equations 3 and 4, one can readily determine the value of N for a textured polycrystalline sample.

Once the total number of grains N within the irradiated volume V has been determined, the average volume of individual grains (Vg) can be correspondingly calculated, as follows:

$$V = N \times Vg \quad \text{(Equation 5)}$$

$$\rightarrow Vg = V/N \quad \text{(Equation 6)}$$

Knowing the average volume of individual grains, average grain size can be calculated based on a modeled assumption of the grain shapes. For example, if all the individual grains are assumed to be ideal spheres of the same size, the diameter of each spherical grain D will be:

$$D = \sqrt[3]{6 \times Vg/\pi} = \sqrt[3]{6 \times V/(\pi N)} \quad \text{(Equation 7)}$$

Knowing the beam size, diffraction geometry, and thickness of the film or material absorption, equation 7 can be rewritten as:

$$D = \sqrt[3]{3 \times a \times b \times t \times p \times \alpha \times f \times \cos\theta \times \Delta\theta/\Delta N} \quad \text{(Equation 8)},$$

In which a and b are the ellipsoid dimensions of the irradiated thickness t. In the special case of thin films (film thickness t<3 microns), the x-rays readily penetrate the entire film and therefore material absorption does not need to be considered.

Other shape models can be assumed besides ideal spheres. For example, using identical cylinder models, the average grain diameter will be:

$$D = \sqrt[3]{2 \times a \times b \times t \times p \times \alpha \times f \times \cos\theta \times \Delta\theta \Delta N} \quad \text{(Equation 9)}$$

The model need not be limited to shapes of only one size, or even only one type of shape. Depending on the actual microstructure that is known to occur in a particular material, one ordinarily skilled in the art can introduce sophisticated models that accurately represent the shape of grains in the material being examined. Accordingly, the invention is capable of being practiced with any of a wide range of models, and is not limited to the above examples, within the skill of the art.

After determining the average grain size, the spot intensity distribution image can be converted into grain size distribution, as for example by the steps of:

(a) plotting the intensity distribution in form of a log-normal graph showing grain count frequency versus natural logarithm of diffraction intensity of each grain; and (b) setting the centroid of the plotted lognormal graph to be the natural logarithm of the average grain size determined.

Additionally, the grain size distribution plot can be converted into a dimensionless size distribution plot, regardless of the actual value of the average grain size determined, by plotting the grain count frequency versus the natural logarithm of each individual grain size divided by the average grain size.

Additional subsets of grain size distribution information can also be provided. Since the crystallographic orientation of each analyzed diffraction spot is known prior to the conversion from $\chi$ and $2\theta$ coordinates to x and y coordinates, the present invention can be used to identify grain size distributions of fiber texture sub-sets of the overall grain population. This requires the registration of orientation information along with the diffraction intensity information associated with each spot. Once the grain size distribution of the entire population has been determined, grain size distribution subsets of particular orientations can be algorithmically identified and plotted.

Although the invention has been variously disclosed herein with reference to illustrative embodiments and features, it will be appreciated that the embodiments and features described hereinabove are not intended to limit the invention, and that other variations, modifications and alternative embodiments will readily suggest themselves to those of ordinary skill in the art. The invention therefore is to be broadly construed, as including such variations, modifications and alternative embodiments, within the spirit and scope of the ensuing claims.

What is claimed is:

1. A method of determining average grain size and grain size distribution of a polycrystalline material, comprising:
    providing a sample comprising said polycrystalline material;
    irradiating a measurement point on the sample with monochromatic radiation energy generated from a radiation source, wherein the beam size and divergence of said radiation energy is adjusted so that an adequate number of crystal grains of said sample is irradiated by the monochromatic radiation energy;
    detecting radiation energy diffracted from the sample to capture a plurality of diffraction arcs within a single data capture frame;
    generating average grain size and grain size distribution data from the diffraction data of the detected diffracted radiation energy, according to an integral grain size analysis protocol comprising the steps of:
        (a) digitally registering raw diffraction data from the plurality of diffraction arcs captured;
        (b) filtering the registered diffraction data to remove background noise, exclude diffraction overlaps or truncations, and compensate for biased data obtained from regions with highly preferred orientations; and
        (c) correlating average grain size and grain size distribution data with the filtered diffraction data.

2. The method of claim 1, wherein the monochromatic radiation energy generated by the radiation source is monochromatic x-radiation.

3. The method of claim 1, wherein the step of detecting radiation energy diffracted from the sample is conducted in proximity to the sample measuring point at a detection locus in fixed spatial relationship to the radiation source.

4. The method of claim 1, wherein the sample is moved only in the sample plane during data acquisition.

5. The method of claim 1, wherein the sample comprises a textured polycrystalline material having grain size ranging from about 0.1 micron to about 100 microns.

6. The method of claim 1, wherein the step of digitally registering the raw diffraction data comprises:
    acquiring and storing the raw diffraction data in the form of a spot intensity distribution image;
    converting the spot intensity distribution image from $\chi$ and $2\theta$ coordinates to x and y coordinates;
    outputting the converted spot intensity distribution image in a three-dimensional surface plot form, with diffraction intensity of each spot registered as spike height at each x and y location.

7. The method of claim 1, wherein the step of filtering the registered diffraction data comprises using minimum intensity criteria to remove background noise.

8. The method of claim 7, wherein a three-dimensional peak-searching algorithm is employed to search for spots meeting the minimum intensity criteria.

9. The method of claim 1, wherein the step of filtering the registered diffraction data comprises fitting said registered diffraction data against a standard distribution function to exclude spots with either excessive intensity overlaps or intensity truncations.

10. The method of claim 9, wherein the standard distribution function comprises a two-dimensional Gaussian curve.

11. The method of claim 1, wherein the step of filtering the registered diffraction data comprises excluding biased data obtained from regions with highly preferred orientations.

12. The method of claim 1, wherein the step of correlating average grain size and grain size distribution data with the filtered diffraction data comprises:
    providing a set of standard polycrystalline samples with known average grain sizes and grain size distributions; and
    calibrating the filtered diffraction data of said sample comprising said polycrystalline material, against the diffraction data of said standard polycrystalline samples, to generate corresponding average grain size and grain size distribution for said sample comprising said polycrystalline material.

13. The method of claim 1, wherein the step of correlating average grain size and grain size distribution data with the filtered diffraction data comprises:
    determining a total number of grains within an irradiated volume of the sample;
    calculating average grain size from the total number of grains within the irradiated volume;
    converting an intensity distribution for the sample into a grain size distribution, based on the average grain size calculated.

14. The method of claim 13, wherein the total number of grains within the irradiation volume of the sample is determined upon mathematically factoring in presence of texture in the sample.

15. The method of claim 13, wherein the intensity distribution is converted into grain size distribution by the steps of:
    plotting the intensity distribution in the form of a lognormal graph showing grain count frequency versus natural logarithm of diffraction intensity of each grain;
    setting the centroid of the planed lognormal graph to be a natural logarithm of the average grain size calculated.

16. The method of claim 15, wherein the grain size distribution is further modified by plotting the grain count frequency versus natural logarithm of grain size of each grain divided by the average grain size calculated.

17. The method of claim 1, wherein the radiation source comprises a collimated x-ray source having means for adjusting beam size and divergence of the generated radiation energy.

18. The method of claim 17, wherein the collimated x-ray source comprises a sealed x-ray beam source, a monochromator, and a tapered capillary collimator.

19. The method of claim 1, wherein the radiation energy diffracted from the sample is detected by a two-dimensional area detector.

20. The method of claim 19, wherein the two-dimensional area detector is position sensitive.

21. The method of claim 19, wherein the two-dimensional area detector comprises means for transfer of detected diffraction data into electronic digital format.

22. The method of claim 19, wherein the two-dimensional area detector is selected from the group consisting of proportional counters, x-ray image charge-coupled device (CCD) cameras, and x-ray image plates.

23. The method of claim 19, wherein the two-dimensional area detector comprises a multiwire gas proportional counter.

24. A crystal grain size analyzing system for determination of average crystal grain size and size distribution of a polycrystalline material, said system comprising:
   a sample comprising said polycrystalline material and defining an associated sample plane;
   a collimated source of monochromatic radiation energy arranged to direct radiation energy to a measurement point on the sample, wherein said collimated source comprises means for adjusting beam size and divergence of the monochromatic radiation energy;
   a 2-dimensional area detector that registers radiation energy diffracted from the sample at the measurement point, said collimated source of monochromatic radiation energy and said 2-dimensional area detector being in a fixed spatial relationship to one another and sufficiently proximate to the sample measuring point to capture a plurality of diffraction arcs within a single data capture frame of said detector;
   a sample motion assembly translating the sample in the sample plane; and
   an integral grain size analysis processor constructed and arranged to generate average grain size and grain size distribution data based on the detected diffraction data of the diffracted energy, wherein said integral grain size analysis processor comprises computational means for:
      (a) digitally registering raw diffraction data from the plurality of diffraction arcs captured;
      (b) filtering the registered diffraction data to remove background noise, exclude diffraction overlaps or truncations, and compensate for biased data obtained from regions of highly preferred orientations; and
      (c) correlating average grain size and grain size distribution data with the filtered diffraction data.

25. The crystal grain size analyzing system of claim 24, wherein the monochromatic radiation energy source emits monochromatic x-radiation.

26. The crystal grain size analyzing system of claim 24, wherein the sample motion assembly is constructed and arranged to permit only in-plane motions of the sample.

27. The crystal grain size analyzing system of claim 24, which does not include any Eulerian cradle providing $\chi$ rotation, or any $\theta$–$2\theta$ goniometer component or apparatus.

28. The crystal grain size analyzing system of claim 24, wherein the sample comprises a textured polycrystalline material having grain size ranging from about 0.1 micron to about 100 microns.

29. The crystal grain size analyzing system of claim 24, wherein the integral grain size analysis processor digitally registers raw diffraction data by the following steps:
   acquiring and storing the raw diffraction data in the form of a spot intensity distribution image;
   converting the spot intensity distribution image from $\chi$ and $2\theta$ coordinates to x and y coordinates;
   outputting the converted spot intensity distribution image in a three-dimensional surface plot form, with diffraction intensity of each spot registered as spike height at each x and y location.

30. The crystal grain size analyzing system of claim 24, wherein the integral grain size analysis processor filters the registered diffraction data by using minimum intensity criteria to remove background noise.

31. The crystal grain size analyzing system of claim 30, wherein the integral grain size analysis processor employs a three-dimensional peak-searching algorithm to search for spots meeting the minimum intensity criteria.

32. The crystal grain size analyzing system of claim 24, wherein the integral grain size analysis processor filters the registered diffraction data by fitting said data against a standard distribution function to exclude spots with either excessive intensity overlaps or intensity truncations.

33. The crystal grain size analyzing system of claim 32, wherein the standard distribution function comprises a two-dimensional Gaussian curve.

34. The crystal grain size analyzing system of claim 24, wherein the integral grain size analysis processor filters the registered diffraction data by excluding biased data obtained from regions with highly preferred orientations.

35. The crystal grain size analyzing system of claim 24, wherein the integral grain size analysis processor correlates average grain size and grain size distribution data with the filtered diffraction data, by providing a set of standard polycrystalline samples with known average grain sizes and grain size distributions, and then calibrating the filtered diffraction data of said sample comprising the polycrystalline material, against the diffraction data of said standard polycrystalline samples, to generate corresponding average grain size and grain size distribution for said sample comprising said polycrystalline material.

36. The crystal grain size analyzing system of claim 24, wherein the integral grain size analysis processor correlates average grain size and grain size distribution data with the filtered diffraction data, by the steps of:
   determining a total number of grains within an irradiated volume of the sample;
   calculating average grain size from the total number of grains within the irradiated volume;
   converting an intensity distribution for the sample into a grain size distribution, based on the average grain size calculated.

37. The crystal grain size analyzing system of claim 36, wherein the integral grain size analysis processor determines total number of grains within the irradiation volume of the sample upon mathematically factoring in presence of texture in the sample.

38. The crystal grain size analyzing system of claim 36, wherein the integral grain size analysis processor converts the intensity distribution into grain size distribution, by plotting the intensity distribution in the form of a log-normal graph showing grain count frequency versus natural logarithm of diffraction intensity of each grain, and setting the centroid of the plotted log-normal graph to be a natural logarithm of the average grain size calculated.

39. The crystal grain size analyzing system of claim 36, wherein the integral grain size analysis processor further modifies the grain size distribution by plotting the grain count frequency versus natural logarithm of grain size of each grain divided by the average grain size calculated.

40. The crystal grain size analyzing system of claim 24, wherein the collimated source comprises a sealed x-ray beam source, a monochromator, and a tapered capillary collimator.

41. The crystal grain size analyzing system of claim 24, wherein the two-dimensional area detector is position sensitive.

42. The crystal grain size analyzing system of claim 24, wherein the two-dimensional area detector comprises means for transfer of detected diffraction data into electronic digital format.

43. The crystal grain size analyzing system of claim 24, wherein the two-dimensional area detector is selected from the group consisting of proportional counters, x-ray image charge-coupled device (CCD) cameras, and x-ray image plates.

44. The crystal grain size analyzing system of claim 24, wherein the two-dimensional area detector comprises a multiwire gas proportional counter.

* * * * *